(12) United States Patent
Kim et al.

(10) Patent No.: US 10,294,453 B2
(45) Date of Patent: May 21, 2019

(54) METHOD FOR INCREASING STEMNESS OF HUMAN MESENCHYMAL STEM CELLS

(71) Applicant: SEOUL NATIONAL UNIVERSITY HOSPITAL, Seoul (KR)

(72) Inventors: Hyo-Soo Kim, Seoul (KR); Eun Ju Lee, Seoul (KR)

(73) Assignee: SEOUL NATIONAL UNIVERSITY HOSPITAL (KR)

(*) Notice: Subject to any disclaimer, the term of this patent is extended or adjusted under 35 U.S.C. 154(b) by 0 days.

(21) Appl. No.: 15/544,619

(22) PCT Filed: Nov. 26, 2015

(86) PCT No.: PCT/KR2015/012751
§ 371 (c)(1),
(2) Date: Nov. 1, 2017

(87) PCT Pub. No.: WO2016/117816
PCT Pub. Date: Jul. 28, 2016

(65) Prior Publication Data
US 2018/0087027 A1    Mar. 29, 2018

(30) Foreign Application Priority Data
Jan. 19, 2015  (KR) .................. 10-2015-0008605

(51) Int. Cl.
| | | |
|---|---|---|
| C12N 5/00 | (2006.01) | |
| C12N 5/074 | (2010.01) | |
| A61K 38/22 | (2006.01) | |
| C12N 5/0775 | (2010.01) | |

(52) U.S. Cl.
CPC ........ *C12N 5/0607* (2013.01); *A61K 38/2285* (2013.01); *C12N 5/0662* (2013.01); *C12N 5/0663* (2013.01); *C12N 2501/998* (2013.01)

(58) Field of Classification Search
CPC ... C12N 5/0607; C12N 5/0662; C12N 5/0663
See application file for complete search history.

(56) References Cited

U.S. PATENT DOCUMENTS

2007/0082394 A1    4/2007    Moscatello

FOREIGN PATENT DOCUMENTS

| KR | 10-0908481 B1 | 7/2009 | |
| WO | 2011129607 A2 * | 10/2011 | ............ A61K 35/28 |

OTHER PUBLICATIONS

Bhartiya. Stem Cell International, vol. 2013, Article ID 547501, 6 pages, http://dx.doi.org/10.1155/2013/547501. 2013 (Year: 2013).*
Kinugawa et al. Journal of Cardiac Failure 9(4):318-324, 2003. (Year: 2003).*
Klyushnenkova et al., "T cell responses to allogeneic human mesenchymal stem cells: immunogenicity, tolerance, and suppression", J Biomed Sci, 2005, vol. 12(1), pp. 47-57.
Le Blanc et al., "Treatment of severe acute graft-versus-host disease with third party haploidentical mesenchymal stem cells", Lancet, 2004, vol. 363(9419), pp. 1439-1441.
Pittenger et al., "Multilineage potential of adult human mesenchymal stem cells", Science, 1999, vol. 284(5411), pp. 143-147.
El-Badri et al., "Osteoblasts promote engraftment of allogeneic hematopoietic stem cells", Experimental Hematology, 1998, vol. 26(2), pp. 110-116, Abstract Only.
Hiyama et al., "Telomere and telomerase in stem cells", British Journal of Cancer, 2007, vol. 96, pp. 1020-1024.
Stanners et al., "Two Types of Ribosome in Mouse-Hamster Hybrid Cells", Nature New Biology, 1971, vol. 230, pp. 52-54.
Morgan et al., "Nutrition of animal cells in tissue culture; initial studies on a synthetic medium", Experimental Biology and Medicine, 1950, vol. 73, pp. 1-8.
Moore et al., "Culture of Normal Human Leukocytes", 1967, The Journal of the American Medical Association, 1967, vol. 199(8), pp. 519-524.
Ham, "Clonal growth of mammalian cells in a chemically defined, synthetic medium", 1965, vol. 53(2), pp. 288-293.
Ham, "An improved nutrient solution for diploid Chinese hamster and human cell lines", Experimental Cell Research, 1963, vol. 29(3), pp. 515-526.
Dulbecco et al., "Plaque production by the polyoma virus", Virology, 1959, vol. 8(3), pp. 396-397.
Barnes et al., "Methods for growth of cultured cells in serum-free medium", Anal. Biochem, 1980, vol. 102, pp. 255-270.
Waymouth, "Rapid proliferation of sublines of NCTC clone 929 (strain L) mouse cells in a simple chemically defined medium (MB 752/1)", J Natl Cancer Inst., 1959, vol. 22(5), pp. 1003-1017.
McCoy et al., "Amino acid requirements of the Novikoff hepatoma in vitro", Proc Soc Exp Biol Med., 1959, vol. 100(1), pp. 115-118.
Ham et al., "Development of improved media and culture conditions for clonal growth of normal diploid cells", In Vitro., 1978, vol. 14(1), pp. 11-22.

* cited by examiner

*Primary Examiner* — Marcia S Noble
(74) *Attorney, Agent, or Firm* — Riverside Law LLP

(57) ABSTRACT

The present invention relates to a method for increasing the stemness of human mesenchymal stem cells and, more particularly, to: a method for increasing the stemness of human mesenchymal stem cells by means of endothelin-1 treatment; the human mesenchymal stem cells having increased stemness by using the method; and a composition for increasing the stemness of human mesenchymal stem cells, containing endothelin-1 as an active ingredient. In the present invention, it is confirmed that the expression of a stemness marker is increased and that a stem cell characteristic is improved such as the length of telomeres being extended, by treating human mesenchymal stem cells with endothelin-1, and thus cellular life span is extended, aging is inhibited, and the growth and viability of cells are increased, thereby enabling mass culturing of human mesenchymal stem cells such that human mesenchymal stem cells are expected to be used effectively in cell therapy or regenerative medicine.

3 Claims, 4 Drawing Sheets
Specification includes a Sequence Listing.

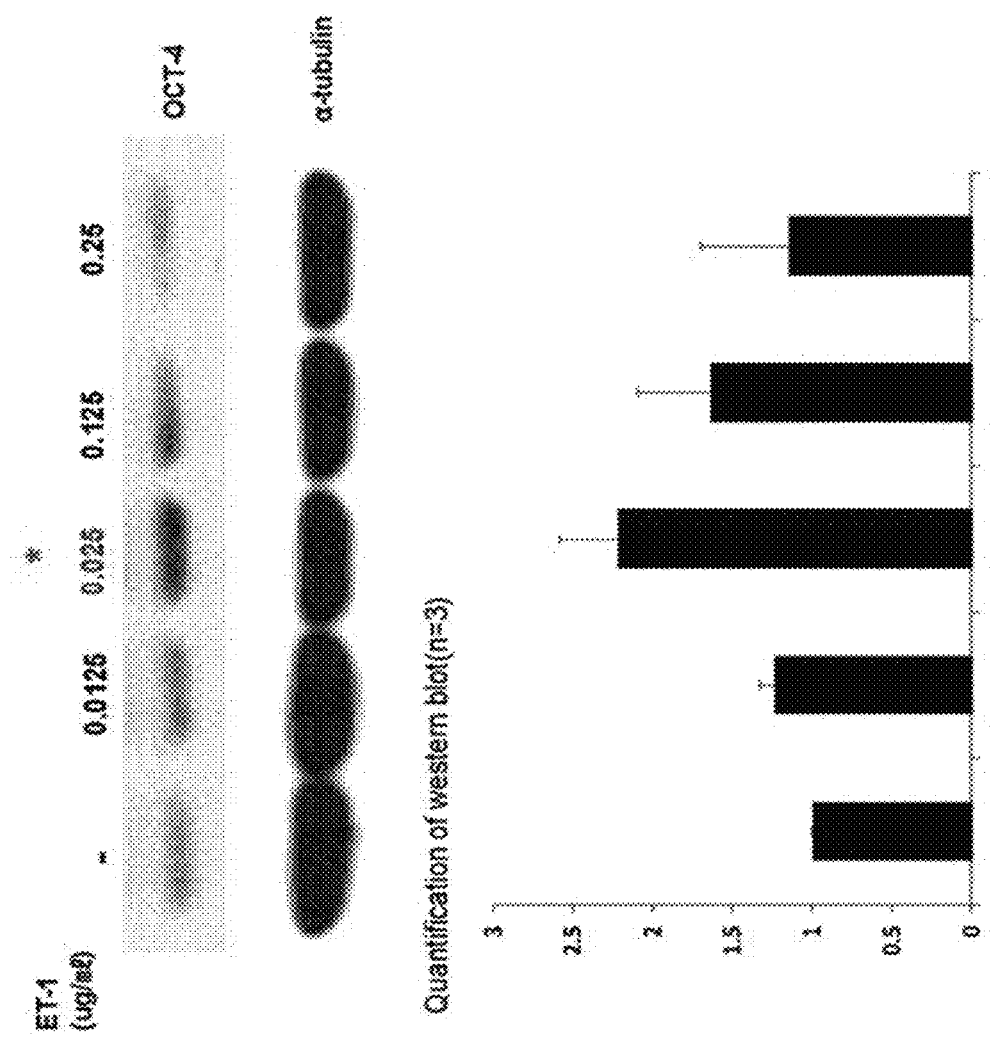
[Fig. 1]

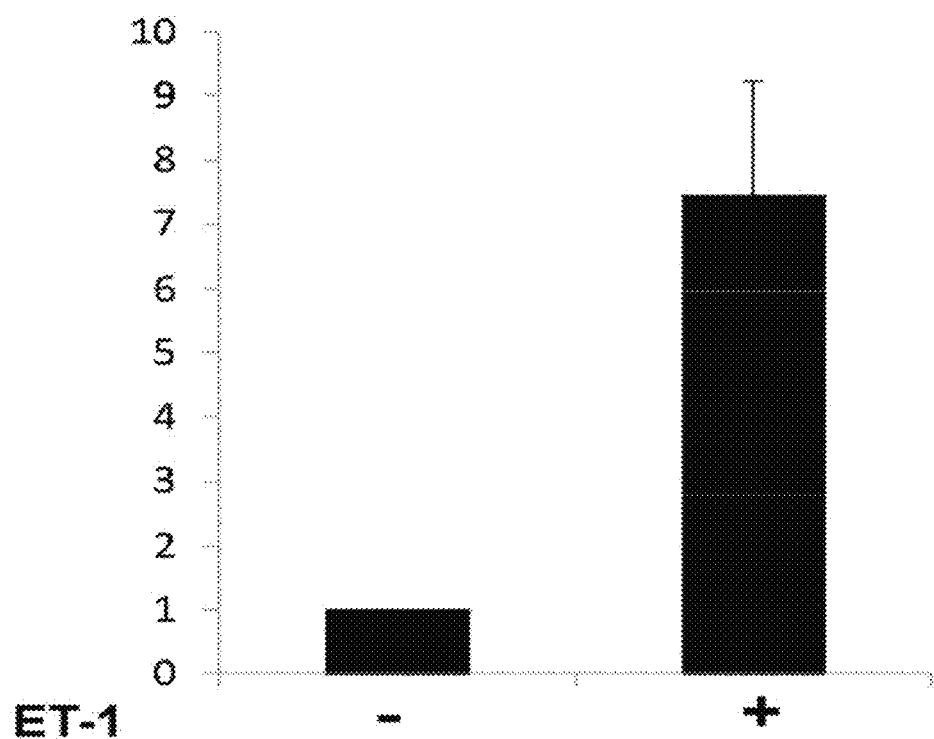
[Fig. 2]

[Fig. 3]
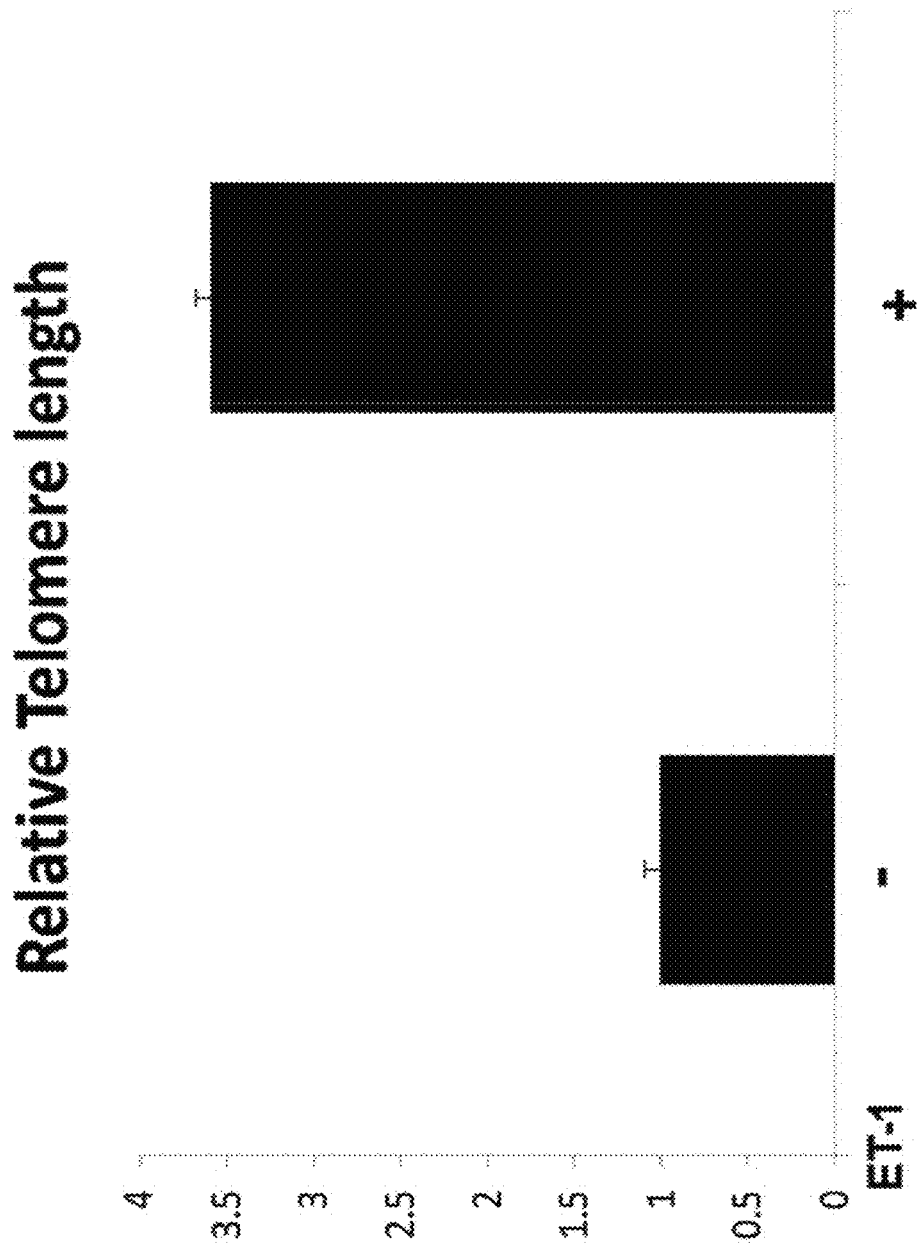

[Fig. 4]
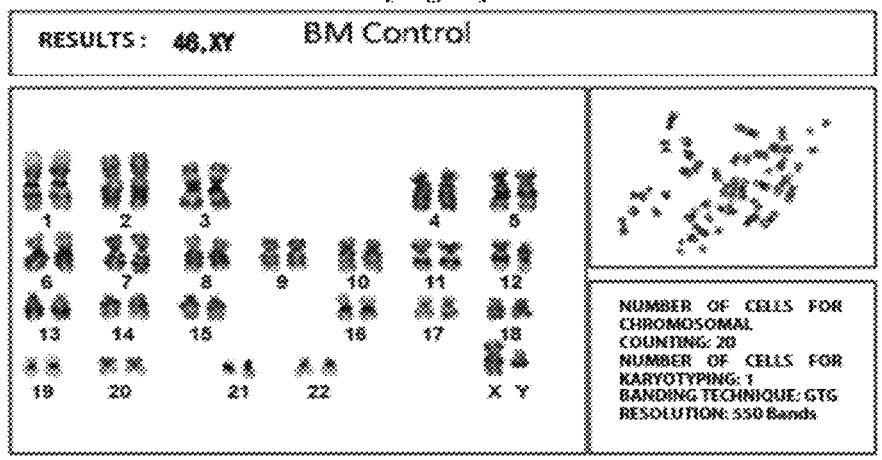
COMMENT
CHROMOSOME ANALYSIS RESULTS SHOW NORMAL KARYOTYPES
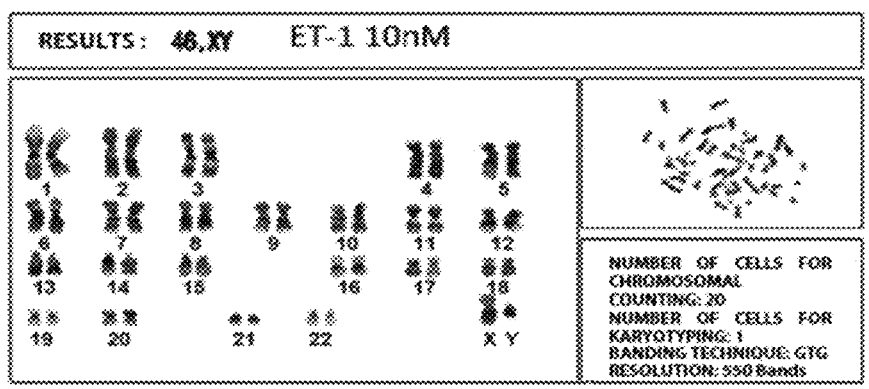
COMMENT
CHROMOSOME ANALYSIS RESULTS SHOW NORMAL KARYOTYPES
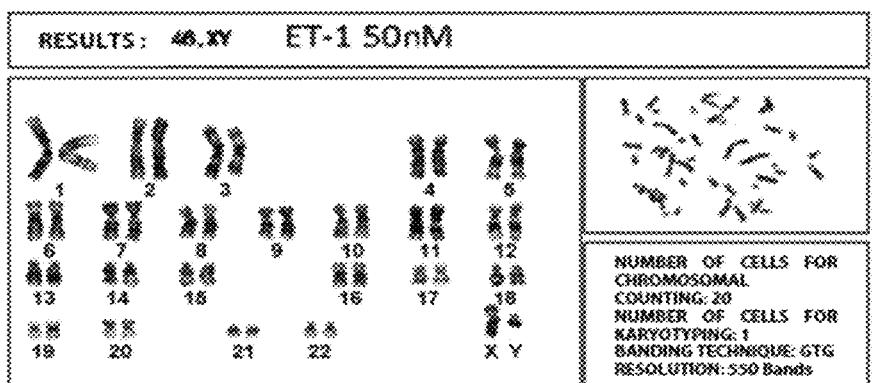
COMMENT
CHROMOSOME ANALYSIS RESULTS SHOW NORMAL KARYOTYPES

```
                        SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Oct4 forward primer

<400> SEQUENCE: 1
gaggcaacct ggagaatttg                                                20

<210> SEQ ID NO 2
<211> LENGTH: 20
<212> TYPE: DNA
<213> ORGANISM: Artificial Sequence
<220> FEATURE:
<223> OTHER INFORMATION: Oct4 reverse primer

<400> SEQUENCE: 2
tagcctgggg taccaaaatg                                                20
```

METHOD FOR INCREASING STEMNESS OF HUMAN MESENCHYMAL STEM CELLS

TECHNICAL FIELD

The present invention relates to a method for increasing stemness of human mesenchymal stem cells and the like.

BACKGROUND ART

Mesenchymal stem cells (MSCs) first found in bone marrow have a high potential as totipotent cells in regenerative medicine. MSCs may be differentiated into various types of in vivo mesoderm lineages, for example, osteocytes, chondrocytes, tendinocytes, adipocytes, myocytes, fibroblasts, and the like. Also, MSCs may be trans-differentiated into nerve cells, myocardial cells, endothelial cells, and interstitial cells under appropriate medium conditions. In addition, bone marrow MSCs express class I MHC antigens other than class II MHC antigens or express co-stimulatory molecules indicating that the MSCs have no immunogenic activities (Klyushnenkova E. et al., J Biomed Sci, 12(1): 47-57, 2005).

In addition, because MSCs exhibit immunosuppressive activities, the MSCs may be used as graft enhancers or inhibitors for fatal graft and host diseases (Le Blanc K et al., Lancet, 363 (9419): 1439-1441, 2004; El-Badri N. S et al., Exp Hematol, 26(2): 110-116, 1998).

Such MSCs may be isolated from various adult tissues such as bone marrow, adipose tissues, cord blood, peripheral blood, neonatal tissues, human placenta, and the like, but have a limitation in the number of MSCs obtained from the adult tissues.

The minimum number of cells required for cell therapy or regenerative medicine is approximately $1 \times 10^9$, and the value thereof further increases when cells used in experiments for establishing conditions and setting criteria are included. To supply this amount of cells from existing MSCs of various origins, the cells should be passaged at least 10 times in vitro. Then, the cells have a problem in that the cells are aged and deformed so that they are not suitable for the concept of therapy any more. This is a major drawback of the existing culture systems for MSCs to be solved. And, even when the conditions and criteria are established for using such cells, there may not be enough of the cells when the cells are used for therapy, and thus MSCs from another human origin often should be used. In this case, additional experiments should be performed for the purpose of using the other cells. Therefore, to use MSCs as a cell therapeutic agent, there is an urgent need for development of a novel method capable of increasing stemness thereof to solve the above problems.

Stemness is generally used in a related art as a meaning generally encompassing pluripotency of stem cells to produce all types of cells such as embryonic stem cells and self-renewal capacity of stem cells to unlimitedly produce self-like cells. Therefore, the stemness may include an ability of stem cells to increase telomerase activity, increase expression of stem cell-mediated factors (stemness-acting signals), increase growth of undifferentiated cells while maintaining the cells in an undifferentiated state, or increase a cell migration activity (Pittenger, M. F. et al. 1999. Multilineage Potential of Adult Human Mesenchymal Stem Cells, Science 284(5411), 143-147).

Meanwhile, endothelin (ET) is a peptide that is produced in vascular endothelial cells and consists of 21 amino acid residues, and is also known as a vasoconstrictor peptide. ET has two S—S bonds in one molecule, and is produced by modifying an ET precursor by means of an ET converting enzyme. ET-1 was first isolated from a culture broth of porcine vascular endothelial cells in 1988, and there are three types of isopeptides (ET-1, ET-2, and ET-3) in most mammals.

ET causes transient vasodilation and sustained vasoconstriction. In this case, the three types of isopeptides have substantially the same effect on the transient vasodilation, and the effect of ET-3 on the vasoconstriction action is approximately one hundredth of those of ET-1 and ET-2. An ET receptor is known to have two types of subtypes. Among these, ETA participates in the vasoconstriction action, and ETB participates in the vasodilation action.

However, it is not yet known whether ET has an effect on the stemness of human MSCs.

DISCLOSURE

Technical Problem

Therefore, the present invention is designed to solve the problems of the prior art, and thus the present inventors have confirmed that endothelin (ET)-1 is an important factor capable of increasing the stemness of human mesenchymal stem cells (MSCs), and have found that ET-1 is applied to solve the prior-art problems such as cell aging caused when MSCs are cultured, and thus may be used to produce cells require for cell therapy and regenerative medicine. Therefore, the present invention has been completed based on the facts.

However, the technical objects of the present invention are not limited thereto, and other objects of the present invention which are not disclosed herein will become more apparent to those of ordinary skill in the art by describing in detail exemplary embodiments thereof.

Technical Solution

To solve the above problems, according to an aspect of the present invention, there is provided a method for increasing stemness of human mesenchymal stem cells. In this case, the method includes treating a culture broth of stem cells with endothelin-1 to culture the stem cells.

According to one exemplary embodiment of the present invention, the method may include treating the culture broth of stem cells with the endothelin-1 at a concentration of 0.0125 to 0.25 µg/mL.

According to another exemplary embodiment of the present invention, the method may include extending a length of telomeres of human mesenchymal stem cells.

According to still another exemplary embodiment of the present invention, the method may include extending a lifespan of human mesenchymal stem cells and inhibiting aging of the human cells.

According to yet another exemplary embodiment of the present invention, the method may include treating the culture broth of the stem cells with the endothelin-1 after 24 hours of an adhesion culture of mesenchymal stem cells.

According to yet another exemplary embodiment of the present invention, the method may include culturing mesenchymal stem cells for 1 to 5 days after the mesenchymal stem cells are treated with the endothelin-1.

According to another aspect of the present invention, there is provided human mesenchymal stem cells having stemness increased through the method.

According to still another aspect of the present invention, there is provided a composition for increasing stemness of human mesenchymal stem cells, which includes endothelin-1 as an active ingredient.

According to one exemplary embodiment of the present invention, the composition may be a cell culture broth.

According to another exemplary embodiment of the present invention, the cells may be human stem cells.

According to still another exemplary embodiment of the present invention, the endothelin-1 may be included at a concentration of 0.0125 to 0.25 µg/mL.

Advantageous Effects

The present invention provides a method for increasing stemness of human mesenchymal stem cells (MSCs), and thus has advantages in that, when MSCs are treated with endothelin-1 (ET-1) according to the present invention, stemness of the MSCs can be increased to culture MSCs in a large scale for a long time, and stem cells whose differentiation potency is maintained can be secured with high yield.

Also, according to the present invention, because it has been identified that ET-1 has an effect of extending a length of telomeres as a cell senescence marker, ET-1 is expected to be applied as an anti-aging factor.

DESCRIPTION OF DRAWINGS

FIG. 1 shows results of determining, through western blotting, a level of expression of an Oct4 protein in human mesenchymal stem cells (MSCs) when the MSCs are treated with endothelin-1 (ET-1).

FIG. 2 shows results of determining, through real time PCR, a level of expression of Oct4 mRNA in human MSCs when the MSCs are treated with ET-1.

FIG. 3 shows results of real time gDNA PCR using gDNA obtained from human MSCs treated with ET-1.

FIG. 4 shows results of determining chromosomal stability of human MSCs treated with ET-1 using a G-banding karyotype analysis method.

BEST MODE

The present invention is characterized by providing a method for increasing stemness of human mesenchymal stem cells (MSCs). For this purpose, the method includes treating a culture broth of stem cells with endothelin-1 (ET-1) to culture the stem cells.

The present inventors have conducted research to solve the prior-art problem of stem cells whose stemness decreases with an increase in the number of passages thereof when human MSCs are passaged, and identified that the stemness of the stem cells is improved when a culture broth of human MSCs is treated with ET-1.

Oct4, Nanog, Sox2, c-Myc, KLF4, and the like have been known as stemness-related markers. Such stemness-related markers have been effectively used for research because it can be seen that stem cells have a higher culture yield and characteristics of the stem cells are more excellently maintained as the stemness-related markers are expressed at a higher level of expression. In particular, Oct4 known to be expressed by undifferentiated stem cells serves to prevent cell differentiation, and is known to disappear when natural differentiation of cells is started. Therefore, a degree of differentiation of the stem cells may be expected depending on a level of expression of Oct4.

According to one exemplary embodiment of the present invention, a culture broth of human MSCs is treated with various concentrations of ET-1, and a expression level of Oct-4 is measured. As a result, it is confirmed that levels of protein and mRNA expression of Oct-4 whose level of expression has decreased increase with an increase in the number of passages (see FIGS. 1 and 2). These results suggest that the stemness of human MSCs is restored when the human MSCs are treated with ET-1. Also, it can be seen that the method of the present invention may be effectively applied to cell therapy and regenerative medicine because it is identified that ET-1 may increase expression of stemness markers such as Oct4 and the like.

Also, a length of telomeres may be determined using another method of determining an improvement of stemness. Telomeres are found at the termini of eukaryotic chromosomes and have a unique structure to prevent chromosomal breakage or end-to-end fusion. Telomeric DNA has a primary structure consisting of tandem repeats of short base sequences (TTAGGG in the case of humans) and has a varying length spanning from several hundreds of base pairs in the case of lower eukaryotic cells to several thousands of base pairs in the case of mammalian cells. A telomeric DNA region has a GC imbalance (GC-rich) as in a centromeric region. When a chromosome is replicated, such a nature of telomeric DNA causes incomplete replication of a G-strand thereof by conventional DNA polymerases so that an exposed complementary strand (C-strand) is degraded by a nucleotide removal enzyme or a telomeric end region thereof may be finished through synthesis using a telomerase. Main functions of telomeres are to cap ends of chromosomes and protect the chromosomes from breakage, end-to-end fusion, and heterologous recombination, which are associated with maintenance of safety of genomes and regulation of growth of cells. Telomere shortening occurs with repeated cell divisions, which activates cell cycle restriction points, which induce replicative senescence and apoptosis, to restrict the growth of cells. The telomere shortening has an advantageous effect of preventing accumulation of genetically unstable cells or altered cells from which cancer arises, but also has an adverse effect of restricting homeostasis of, regeneration of, and survival of organs when the aging and diseases occur. A decline in tissue regeneration function due to telomere shortening is associated with stem cell dysfunction, and telomere dysfunction induces impaired functions of stem cells by not only activating the stem cells' own restriction points but also changing all micro- and macro-environments surrounding the stem cells (E Hiyama et al., British Journal of Cancer, 96: 1020-1024, 2007).

Therefore, according to one exemplary embodiment of the present invention, after adhesion-cultured MSCs are treated with ET-1 and cultured for 24 hours or more, a length of telomeres thereof is compared to that of a group (control) in which MSCs are not treated with ET-1. As a result, it is confirmed that, when the human MSCs are treated with ET-1, the length of the telomeres, that is, end regions of chromosomes, may be extended (see FIG. 3), and the ET-1 treatment causes no chromosomal abnormality (see FIG. 4). From the results, it can be seen that, when human MSCs are treated with ET-1, a length of telomeres thereof may be extended to extend the lifespan of the stem cells, inhibit aging of the stem cells, and enhance growth and viability of the stem cells, which makes it possible to culture stem cells in a large scale in order to overcome conventional limitations in in vitro culture of human MSCs.

Therefore, the present invention may provide a method for increasing stemness of human MSCs, which includes treating human MSCs with ET-1, and human MSCs having increased stemness using the method. Increasing the stemness of MSCs means that the MSCs have a high potential of differentiating into various mesoderm lineage cells such as bones, tendons, muscles, and the like. Accordingly, MSCs are expected to be a cell therapeutic agent applicable to a wider range of diseases. Also, the present invention may provide a composition for increasing stemness of human MSCs, which includes ET-1 as an active ingredient.

In the present invention, the term "cell culture broth" refers to a culture broth of human MSCs. Here, the human MSCs may be derived from various tissues and pluripotent stem cells of human bodies, such as bone marrow, adipose tissues, cord blood, peripheral blood, neonatal tissues, human placenta, and the like. The human MSCs are preferably derived from bone marrow, but the present invention is not limited thereto.

In the present invention, the term "stem cell" refers to a cell that may differentiate into various cells constituting biological tissues, and thus generally includes undifferentiated cells that may be regenerated in an unrestricted manner to form specialized cells in tissues and organs. The stem cells are developmental pluripotent or multipotent cells. The stem cells may divide to produce two daughter stem cells or produce one daughter stem cell and one progenitor ("transit") cell, which then proliferate into fully differentiated and mature cells in tissues.

The term "cell culture broth" used in the present invention refers to a medium containing cultured cells, and the term "medium" refers to a medium for animal cells generally used in the related art. Any medium generally used for animal cell culture may be used as the medium that may be used in the present invention. For example, an Eagle's minimum essential medium (MEM) (Eagle, H. Science 130: 432 (1959)), α-MEM (Stanner, C. P. et al., Nat. New Biol. 230: 52 (1971)), Iscove's MEM (Iscove, N. et al., J. Exp. Med. 147: 923 (1978)), Medium 199 (Morgan et al., Proc. Soc. Exp. Bio. Med., 73: 1 (1950)), CMRL 1066, RPMI 1640 (Moore et al., J. Amer. Med. Assoc. 199: 519 (1967)), F12 (Ham, Proc. Natl. Acad. Sci. USA 53: 288 (1965)), F10 (Ham, R. G. Exp. Cell Res. 29: 515 (1963)), a Dulbecco's modification of Eagle's medium (DMEM: Dulbecco, R. et al., Virology 8: 396 (1959)), a mixture of DMEM and F12 (Barnes, D. et al., Anal. Biochem. 102: 255 (1980)), Waymouth's MB752/1 (Waymouth, C. J. Natl. Cancer Inst. 22: 1003 (1959)), McCoy's 5A (McCoy, T. A., et al., Proc. Soc. Exp. Biol. Med. 100: 115 (1959)), MCDB series (Ham, R. G. et al., In Vitro 14: 11 (1978)), and the like may be used. Therefore, the medium may be preferably selected from the group consisting of α-MEM, Eagles's MEM, Iscove's MEM, Medium 199, CMRL 1066, RPMI 1640, F12, F10, DMEM, Way-mouth's MB752/1, and McCoy's 5A. Most preferably, the medium may be an α-MEM medium, but the present invention is not limited thereto. The medium of the present invention may further include a serum. In addition to the serum, the medium of the present invention may include any components known in the related art for a conventional composition for culturing stem cells to effectively culture the stem cells.

Also, in the present invention, ET-1 is preferably included in the medium at a concentration of 0.0125 to 0.25 μg/mL, is more preferably included in the medium at a concentration of 0.02 to 0.09 μg/mL, and is most preferably included in the medium at a concentration of 0.02 to 0.03 μg/mL, but the present invention is not limited thereto.

Hereinafter, preferred examples are provided to aid in understanding the present invention. However, it should be understood that detailed description provided herein is merely intended to provide a better understanding of the present invention and is not intended to limit the scope of the present invention.

EXAMPLES

Example 1: Confirmation of Effect of ET-1 Treatment on Increase in Stemness of Human MSCs To check whether ET-1 increased stemness of human MSCs, expression of the most common marker Oct4 as a stemness-related factor was examined.

1-1. Confirmation of Western Blotting Results

To determine a level of expression of an Oct4 protein in human MSCs when the human MSCs were treated with ET-1, human MSCs purchased from Lonza were treated with an increasing concentration (0, 0.0125, 0.025, 0.125, and 0.25 μg/mL) of ET-1, and a level of protein expression was determined through western blotting. In this case, types of primary and secondary antibodies used and a dilution ratio thereof are listed in the following Table 1.

TABLE 1

| Protein | Size (kDa) | Primary Antibody | Secondary Antibody | ECL |
| --- | --- | --- | --- | --- |
| Oct4 | 43 | Santacruz anti-Oct4 antibody sc-9081 1:2,000 Dilution | Anti-goat IgG (whole molecule)-peroxidase antibody produced in rabbit (Sigma-Aldrich A5420) 1:3,000 dilution | Approximately 7 minutes |
| Positive control (α-tubulin) | 55 | 1:10,000 Dilution | Anti-mouse IgG (whole molecule)-peroxidase antibody produced in goat (Sigma-Aldrich A4416) 1:23,000 dilution | Approximately 5 seconds |

As a result, it can be seen that the level of protein expression of the stemness marker Oct4 was significantly increased when the human MSCs were treated with ET-1, particularly the Oct4 had the highest level of protein expression when the human MSCs were treated with ET-1 at a concentration of 0.025 μg/mL, as shown in FIG. 1.

1-2. Confirmation of Real Time PCR Results

To compare levels of mRNA expression of Oct4 in human MSCs treated with ET-1, the human MSCs were treated with ET-1, and RNA was extracted therefrom after 24 hours to synthesize complementary cDNA. Thereafter, real time PCR was performed using the complementary cDNA as a template and Oct4 amplification primers set forth in the following SEQ ID NOs: 1 and 2.

SEQ ID NO: 1: 5'-gaggcaacct ggagaatttg-3' (Oct4 forward primer)

SEQ ID NO: 2: 5'-tagcctgggg taccaaaatg-3' (Oct4 reverse primer)

As a result, it was confirmed that the mRNA expression of Oct4 increased when the human MSCs were treated with ET-1, as shown in FIG. 2.

Example 2: Confirmation of Change in Length of Telomeres in Human MSCs Through ET-1 Treatment To check a change in a length of telomeres in human MSCs when the human MSCs were treated or were not treated with ET-1, the human MSCs were prepared so that the cells reached a confluency of 60% on a 60 mm plate. Before the human MSCs were treated with ET-1, a culture broth was replaced with a fresh culture broth. Thereafter, the human MSCs were treated with 0.025 μg/mL of ET-1, and the medium was replaced with a fresh culture broth after 24 hours. After 3 days, gDNA samples were collected. Then, real time gDNA PCR was performed using the samples to compare the lengths of the telomeres by means of ET-1 treatment.

As a result, it was confirmed that the lengths of the telomeres were extended approximately three-fold or more when the human MSCs were treated with ET-1, as shown in FIG. 3.

Example 3: Confirmation of Chromosomal Stability in Human MSCs Treated with ET-1

Because the lengths of the telomeres were extended when the human MSCs from Example 2 were treated with ET-1, chromosomal stability thereof was checked using a G-banding karyotype analysis method in which chromosomal dysfunction was not induced. For this purpose, the G-banding karyotype analysis method known as a basic test method for evaluating genomic stability was performed. The G-banding karyotype analysis method is a method of pre-treating stem cells with trypsin, which is a proteolytic enzyme, and staining chromosomes with a Giemsa stain. In this case, euchromatin is stained with a light color, and heterochromatin is stained with a dark color. The G-banding karyotype analysis method is the test method most often used for chromosomal analysis because many staining bands are generated.

As a result of the G-banding karyotype analysis, it was confirmed that chromosomal dysfunction was not induced when the human MSCs were treated with ET-1, as shown in FIG. 4.

Although the present invention presented herein has been disclosed for illustrative purposes, it should be apparent to those skilled in the art to which the present invention belongs that various modifications and changes are possible without departing from the scope and spirit of the present invention. Therefore, it should be understood that the exemplary embodiments disclosed above are illustrative in all aspects and are not intended to limit the present invention.

The invention claimed is:

1. A method for extending telomere length in human mesenchymal stem cells, comprising: treating a culture broth of human mesenchymal stem cells with endothelin-1 at a concentration of 0.026 to 0.125 μg/mL to culture the human mesenchymal stem cells.

2. The method of claim 1, wherein the stem cells treated with endothelin-1 comprise an increased lifespan of human mesenchymal stem cells.

3. The method of claim 1, wherein the method comprises treating the culture broth of the stem cells with the endothelin-1 after 24 hours of an adhesion culture of the mesenchymal stem cells.

* * * * *